(12) United States Patent
Weiner et al.

(10) Patent No.: US 7,455,841 B2
(45) Date of Patent: Nov. 25, 2008

(54) GENETIC CONSTRUCTS AND COMPOSITIONS COMPRISING RRE AND CTE AND USES THEREOF

(75) Inventors: David B. Weiner, Merion, PA (US); Karuppiah Muthumani, Cherry Hill, NJ (US)

(73) Assignee: The Trustees of the University of Pennsylvania, Philadephia, PA (US)

( * ) Notice: Subject to any disclaimer, the term of this patent is extended or adjusted under 35 U.S.C. 154(b) by 242 days.

(21) Appl. No.: 10/535,326

(22) PCT Filed: Nov. 19, 2003

(86) PCT No.: PCT/US03/36924

§ 371 (c)(1),
(2), (4) Date: Feb. 2, 2006

(87) PCT Pub. No.: WO2004/045548

PCT Pub. Date: Jun. 3, 2004

(65) Prior Publication Data

US 2006/0140978 A1 Jun. 29, 2006

Related U.S. Application Data

(60) Provisional application No. 60/427,856, filed on Nov. 19, 2002.

(51) Int. Cl.
*A61K 39/00* (2006.01)
(52) U.S. Cl. .................................. 424/184.1
(58) Field of Classification Search .............. None
See application file for complete search history.

(56) References Cited

U.S. PATENT DOCUMENTS

| 5,554,528 A | 9/1996 | Harrison et al. |
| 5,585,263 A | 12/1996 | Hammarskjold et al. |
| 5,593,972 A | 1/1997 | Weiner et al. |
| 5,604,114 A | 2/1997 | Haseltine et al. |
| 5,650,309 A | 7/1997 | Wong-Staal et al. |
| 5,665,577 A | 9/1997 | Sodroski et al. |
| 5,739,118 A | 4/1998 | Carrano et al. |
| 5,880,276 A | 3/1999 | Hammarskjold et al. |
| 5,981,505 A | 11/1999 | Weiner et al. |
| 6,057,095 A | 5/2000 | Arrigo |

FOREIGN PATENT DOCUMENTS

WO  WO 94/16737  8/1994

OTHER PUBLICATIONS

Zolotukhin et al., Continuous Propagation of RRE(−) and Rev(−)RRE(−) Human Immunodeficiency Virus Type 1 Molecular Clones Containing a cis-Acting Element of Simian Retrovirus Type 1 in Human Peripheral Blood Lymphocytes, Journal of Virology, 1994, 68(12):7944-7952.*
Ernst et al. "Secondary structure and mutational analysis of the Mason-Pfizer monkey virus RNA constitutive transport element," *RNA* (1997) 3(2):210-222.
Saavedra et al., "The simian retrovirus-1 constitutive transport element, unlike the HIV-1 RRE, uses factors required for cellular mRNA export," *Curr Biol* (1997) 7(9):619-628.
Bray et al., "A small element from the Mason-Pfizer monkey virus genome makes human immunodeficiency virus type 1 expression and replication Rev-independent," *Proc Natl Acad Sci USA* (1994) 91(4):1256-1260.
Kang et al., "Analysis of cellular factors that mediate nuclear export of RNAs bearing the Mason-Pfizer monkey virus constitutive transport element," *J Virol* (2000) 74(13):5863-5871.
Srinivasakumar et al., "Novel Tat-encoding bicistronic human immunodeficiency virus type 1-based gene transfer vectors for high-level transgene expression," *J of Virology* (2000) 74(14):6659-6668.
Srinivasakumar et al., "A lentivirus packaging system based on alternative RNA transport mechanisms to express helper and gene transfer vector RNAs and its use to study the requirement of accessory proteins for particle formation and gene delivery," *J of Virology* (1999) 73(11):9589-9598.
Wodrich et al., "A new RNA element located in the coding region of a murine endogenous retrovirus can functionally replace the Rev/Rev-responsive element system in human immunodeficiency virus type 1 Gag expression," *J of Virology* (2001) 75(22):10670-10682.

(Continued)

*Primary Examiner*—Bruce Campell
*Assistant Examiner*—Nicole Kinsey White
(74) *Attorney, Agent, or Firm*—Pepper Hamilton LLP

(57) ABSTRACT

Genetic constructs that comprise a coding sequence for HIV-1 Rev, and a coding sequence for a desired protein are disclosed. Compositions that comprise at least two nucleic acid molecules in which at least one nucleic acid molecule comprises a coding sequence for HIV-1 Rev, and at least one nucleic acid molecule comprises a coding sequence for a desired protein are disclosed. In such genetic constructs and compositions comprising nucleic acid molecules, the coding sequence for the desired protein comprises at least a portion of coding sequence for an HIV structural protein that includes an RRE and at least one CTE. Methods of inducing an immune response against an immunogen in an individual, methods of delivering proteins to an individual and methods of producing proteins are also disclosed.

30 Claims, 5 Drawing Sheets

OTHER PUBLICATIONS

Wodrich et al., "Multiple copies of the Mason-Pfizer monkey virus constitutive RNA transport element lead to enhanced HIV-1 Gag expression in a context-dependent manner," *Nucleic Acids Research* (2000) 28(4):901-910.

Rizvi et al., "Role of Mason-Pfizer monkey virus (MPMV) constitutive transport element (CTE) in the propagation of MPMV vectors by genetic complementation using homologous/heterologous env genes," *Virology* (1996) 224(2):517-532.

* cited by examiner

T-cell proliferative response to Env

Induction of intracellular IFN-γ in vaccinated spelenocytes

Comparison of EAC-1 and EAC-II

Induction of intracellular IFN-γ in vaccinated spleenocytes
Comparison of EAC-1 and Codon optimized Clade B

GENETIC CONSTRUCTS AND COMPOSITIONS COMPRISING RRE AND CTE AND USES THEREOF

CROSS-REFERENCE TO RELATED APPLICATIONS

This application is a national stage application of PCT International Application PCT/US2003/036924, filed Nov. 19, 2003, which claims priority to U.S. Provisional Patent Application 60/427,856, filed Nov. 19, 2002.

FIELD OF THE INVENTION

The present invention relates to improved genetic constructs. In particular, the present invention relates to nucleic acid molecules that can be used to generate high levels of expression of proteins encoded by nucleic sequences of the nucleic acid molecule. The present invention also relates to improved DNA vaccines and gene therapeutics.

BACKGROUND OF THE INVENTION

The HIV-1 Rev-RRE is well known but not completely understood. It is known that genes encoding HIV structural proteins, i.e. HIV genes gag, pol and env each contain an RRE which is recognized by HIV protein Rev. These sequences are known to interact with the HIV protein Rev. Nucleic acid molecules in cells that contain the RRE bind to Rev that is present in the cell and are transported to the cytoplasm. This transport results in a higher level of gene expression relative to that observed in the absence of the RRE or Rev in similar constructs. U.S. Pat. Nos. 5,554,528 and 5,604,114, which are incorporated herein by reference, disclose HIV RRE sequences. U.S. Pat. Nos. 5,650,309 and 5,665,577, which are incorporated herein by reference, disclose vectors that comprise HIV RRE sequences.

The CTE system is well known and described in, inter alia, U.S. Pat. Nos. 5,585,263 and 5,880,276, which are each incorporated herein by reference. According to this system, host proteins recognize the CTE sequence on the mRNA and transport it from the nucleus to the cytoplasm. This transport results in a higher level of gene expression relative to that observed in the absence of the RRE or Rev in similar constructs. CTE systems are also described in Bray, M., S. Prasad, J. W. Dubay, E. Hunter, K.-T. Jeang, D. Rekosh, and M.-L. Hammarskjold (1994). A small element from the Mason-Pfizer monkey virus genome makes human immunodeficiency virus type 1 expression and replication Rev-independent. Proc. Natl. Acad. Sci. USA 91:1256-1260; Saavedra, C., B. Felber, and E. Izaurralde. 1997. The simian retrovirus-1 constitutive transport element, unlike the HIV-1 RRE, utilises factors required for the export of cellular mRNAs. Curr. Biol. 619-628, Ernst R K, Bray M, Rekosh D, Hammarskgold M L. (1997) Secondary structure and mutational analysis of the Mason-Pfizer monkey virus RNA constitutive transport element. RNA. 3(2):210-22; and Kang Y, Bogerd H P, Cullen B R. (2000). Analysis of cellular factors that mediate nuclear export of RNAs bearing the Mason-Pfizer monkey virus constitutive transport element. J Virol. 74(13):5863-71, which are each incorporated herein by reference.

There is a need to provide improved systems for enhancing expression of coding sequences in nucleic acid molecules. There is a need to provide improved vaccines, immunization methods, and gene therapy methods and compositions that exhibit high levels of expression of coding sequences in nucleic acid molecules.

SUMMARY OF THE INVENTION

The present invention relates to genetic constructs that comprise a coding sequence for HIV-1 Rev, and a coding sequence for a desired protein. In such genetic constructs, the coding sequence for the desired protein comprises at least a portion of coding sequence for an HIV structural protein that includes an RRE and at least one CTE.

The present invention also relates to compositions that comprise at least two nucleic acid molecules in which at least one nucleic acid molecule comprises a coding sequence for HIV-1 Rev, and at least one nucleic acid molecule comprises a coding sequence for a desired protein. The coding sequence for the desired protein comprises at least a portion of coding sequence for an HIV structural protein that includes an RRE and at least one CTE. The desired protein is generally a different protein from HIV-1 Rev.

The present invention further relates to methods of inducing an immune response against an immunogen in an individual. Some of the methods of the invention comprise the step of administering to the individual a genetic construct comprising coding sequence for HIV-1 Rev, and coding sequence for an immunogen. The coding sequence for the immunogen comprises at least a portion of coding sequence for an IV structural protein that includes an RRE and at least one CTE. Some of the methods of the invention comprise the step of administering to the individual a composition comprising at least two nucleic acid molecules. At least one nucleic acid molecule comprises a coding sequence for HIV-1 Rev, and at least one nucleic acid molecule comprises a coding sequence for an immunogen. The coding sequence for the immunogen comprises at least a portion of coding sequence for an HIV structural protein that includes an RRE and at least one CTE.

The present invention further relates to methods of delivering a protein to an individual. Some of the methods of the invention comprise the step of administering to the individual a genetic construct comprising coding sequence for HIV-1 Rev, and coding sequence for an protein. The coding sequence for the protein comprises at least a portion of coding sequence for an HIV structural protein that includes an RRE and at least one CTE. Some of the methods of the invention comprise the step of administering to the individual a composition comprising at least two nucleic acid molecules. At least one nucleic acid molecule comprises a coding sequence for HIV-1 Rev, and at least one nucleic acid molecule comprises a coding sequence for a desired protein. The coding sequence for the protein comprises at least a portion of coding sequence for an HIV structural protein that includes an RRE and at least one CTE.

The present invention further relates to methods of producing a protein in a cell. Some of the methods of the invention comprise the step of culturing a cell that comprises a genetic construct comprising coding sequence for HIV-1 Rev, and coding sequence for an protein. The coding sequence for the protein comprises at least a portion of coding sequence for an HIV structural protein that includes an RRE and at least one CTE. Some of the methods of the invention comprise the step of culturing a cell comprising at least two nucleic acid molecules. At least one nucleic acid molecule comprises a coding sequence for HIV-1 Rev, and at least one nucleic acid molecule comprises a coding sequence for a desired protein. The coding sequence for the protein comprises at least a portion of coding sequence for an HIV structural protein that includes an RRE and at least one CTE.

DESCRIPTION OF THE INVENTION

Figure 1:
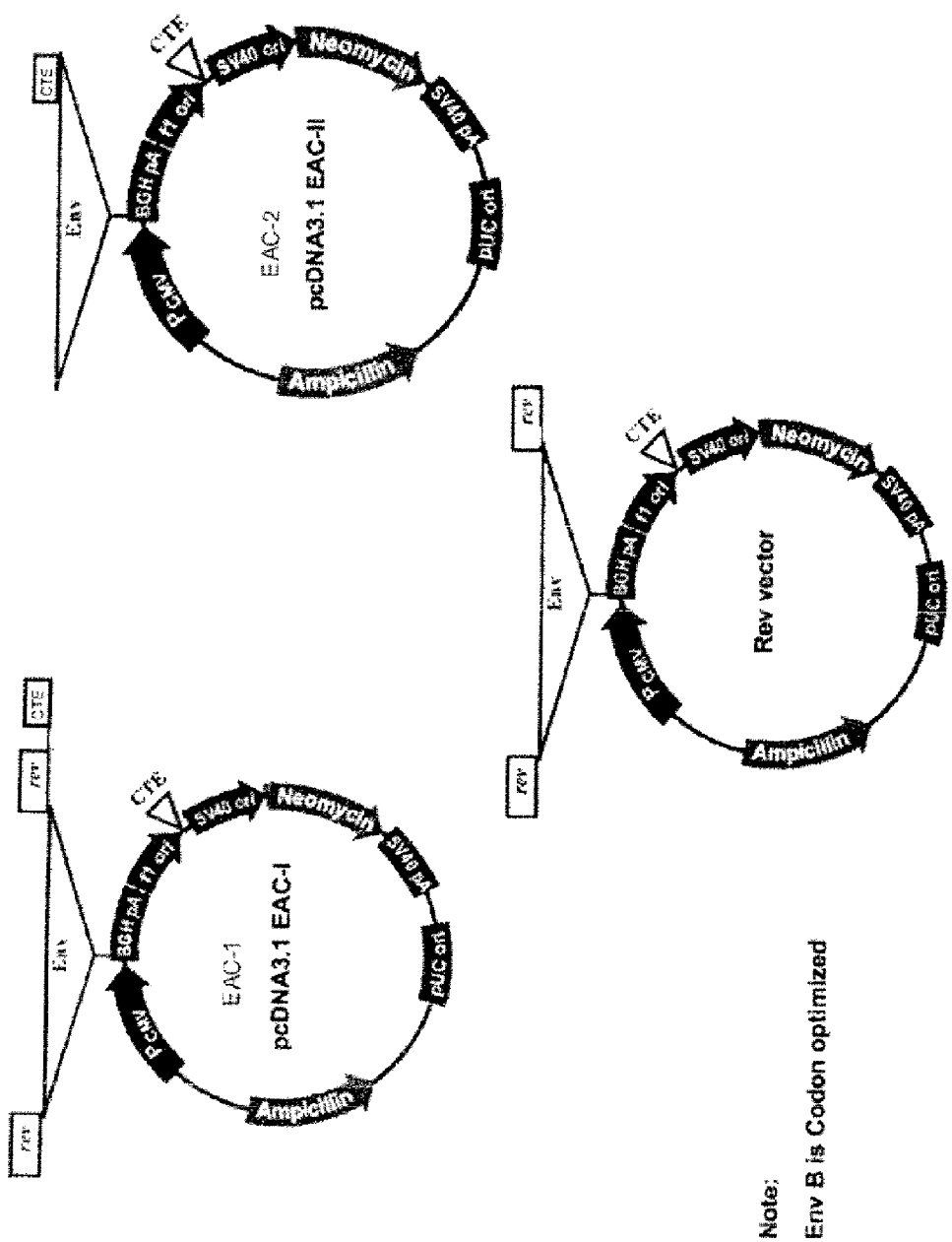
FIGS. 1-5 show data from comparisons made between the immune responses against HIV-1 Env following administration of one of three plasmids, each of which encode Env in which the Env coding sequence contains the RRE. These data are described in the Example below.

According to the invention, nucleic acid molecules are supplied with two different transport elements which when present on mRNA result in the shuttling of the mRNA from the nucleus to the cytoplasm and protein production in the cell is increased. The two transport elements operate independent of one another and when used together result in a higher enhancement of protein production than simply an additive effect.

Each of the transport systems employed is known. One is the HIV-1 Rev-Rev response element (RRE) system. The other is the CTE system isolated from Mason Pfizer Monkey Virus. According to the invention, genetic constructs contain both an RRE and at least one CTE. Furthermore, the constructs are provided with HIV-1 Rev-encoding sequences to provide the cell with the Rev protein needed to engage the RRE and effect transport.

As used herein, the term "genetic construct" is meant to refer to a nucleic acid molecule that comprises a nucleic acid sequence that encodes a protein (coding sequence) operably linked to elements necessary for expression of the coding sequence. In some embodiments, the genetic construct is DNA, preferably a plasmid or genome of a viral vector. In some embodiments, the genetic construct is RNA, preferably a genome of a retroviral vector.

According to the present invention, genetic constructs are provided which comprise coding sequence for Rev, and a coding sequence for a desired protein. As used herein, the term "desired protein: is meant to refer to any protein, including proteins with physiologically or immunogenically active sequences, provided such protein comprises at least a portion of coding sequence for an HIV structural protein that includes an RRE and the mRNA that includes a coding sequence for the protein comprises at least one CTE. In some embodiments, the desired protein is an HIV structural protein and the mRNA that includes a coding sequence for the HIV structural protein comprises at least one CTE. In some embodiments, the desired protein is a fusion protein comprising at least a portion an HIV structural protein and a non-HIV portion. In some embodiments, the non-HIV portion may be an immunogenically or physiologically active protein or immunogenically or physiologically active fragment thereof that further comprises an HIV structural protein or fragment thereof that comprises a RRE. If the desired protein is not an HIV structural protein, i.e. it is a fusion protein, the nature of non-HIV sequences will determine if the genetic construct is a vaccine or a gene therapeutic. That is, if the fusion protein that is the desired protein is an immunogen, the construct may be used to induce immune responses such as a use as a vaccine, or a starting material for protein production. If the fusion protein is biologically active and non-immunogenic, the construct may be used a gene therapeutic or a starting material for protein production.

The invention also provides a composition with at least two nucleic acid molecules, at least one of which comprises a coding sequence for HIV-1 Rev, and at least one of which comprises a coding sequence for a desired protein. In some embodiments, nucleic acid molecules are DNA molecules, preferably plasmids.

The genetic constructs of the invention and nucleic acid molecules of compositions of the invention include a coding sequence selected from the group consisting of gag, pol, env, and a fragment thereof which include an RRE. That is, the invention can be used for high level expression of the HIV proteins encoded by of gag, pol, or env, or alternatively, they can be used for high level expression of fusion proteins that include portions of gag, pol, or env gene products that include the RRE. The genetic construct also contains coding sequences that encode HIV-1 Rev protein operably linked to regulatory elements so that the Rev protein is produced. The compositions contains a nucleic acid molecule that comprises the coding sequences that encode HIV-1 Rev protein operably linked to regulatory-elements so that the Rev protein is produced.

According to the invention, the CTE sequence or sequences are included in the gene construct or nucleic molecule of a composition in the sequence of the protein to be produced. In preferred embodiments, the CTE sequence is included at a site 3' of the polyadenylation tail. In some embodiments, the gene construct may contain more than one CTE sequences. In some embodiments, it may contain 2, 3, 4 or 5 CTE sequences.

The present invention further provides methods of inducing an immune response against an immunogen in an individual, methods of delivering a protein to an individual and methods of producing a protein.

The methods of inducing an immune response against an immunogen in an individual and the methods of delivering a protein to an individual comprising the step of administering to the individual a genetic construct or composition as described above. In the methods of inducing immune responses, the desired protein is immunogenic. If the desired protein is an HIV structural protein, the genetic construct is a vaccine and the desired protein is expressed for the purpose of being an immunogen. Similarly, if the desired protein is an immunogenic protein, the genetic construct or composition can be used as a vaccine and the desired protein is expressed for the purpose of being an immunogen. Immune responses may be induced to provide protective or therapeutic effects or to produce antibodies and antigen specific immune system cells specific for the immunogen. Such antibodies and cells may be collected and used.

Examples of immunogens that can be encoded by the present invention include the HIV structural proteins Gag, Pol, Env, and fragments thereof. In addition, vaccines may be prepared in which the immunogen is a target protein as described in U.S. Pat. No. 5,593,972 issued Jan. 14, 1997 that is incorporated herein by reference. Such immunogens may be pathogen proteins, proteins associated with hyperproliferative diseases or proteins associated with autoimmune diseases as well as allergens. For all non-HIV structural protein immunogens, the immunogenic protein must be presented as a fusion protein encoded by a chimeric gene which includes coding sequence that includes at least the portion of the HIV structural protein coding sequence which is the RRE. In embodiments of the invention in which an immune response is delivered, the present invention may be used in combination with adjuvants, immunomodulating proteins and genetic sequences that encode immunomodulating proteins such as cytokines, chemokines, and growth factors.

The methods of delivering a protein to an individual comprise the step of administering to the individual a genetic construct or composition as described above. In some embodiments, the desired protein is a cytokine, a growth factor, a chemokine, a co-stimulatory molecule, an antibody, a soluble receptor, an enzyme, a coagulation factor, or fragments thereof. In some embodiments, the desired protein is a pathogen antigen, an oncogene translation product or other antigen associated with cancer, a protein associated with autoimmune disease, an allergen or fragments thereof. In some embodiments, the desired protein is insulin, IL-1, IL-2, IL-5, IL-12, IL-15, VEGF, EGF, EPO, GMCSF, GCSF, receptors thereof, CD28, CD80, CD86, CD40, CD40L, mAbs, Fabs, F(ab)$_2$s, chimeric, humanized, primatized, human mAbs, Fabs, F(ab)$_2$s, DNAse, tPA, Factors I-XII, or active fragments thereof. In some embodiments, the desired protein is an antigen as set forth in U.S. Pat. No. 5,593,972 which is incorporated herein by reference.

The methods of producing a protein in a cell comprise the step of culturing a cell that comprises a genetic construct or at least two nucleic acid molecules of the composition as described above. In such methods, the cell may be any cell in which both the RRE system and CTE system are active. In some embodiments, the cell is a mammal cell. In some embodiments, the cell is a human cell.

In preferred embodiments, the genetic constructs are plasmids that may be delivered to the patient by direct administration. There are a large number of methods that can be used to deliver DNA directly to a patient. In addition to those described in U.S. Pat. No. 5,593,972, which is incorporated herein by reference, other methods include those described in U.S. Pat. No. 5,739,118 which is incorporated herein by reference, and U.S. Pat. No. 5,981,505 which is incorporated herein by reference. In addition, the methods described in the patents and publications disclosed in <www.dnavaccine.com>, which are each incorporated herein by reference, may be employed using the improvements described herein. For example, the invention is compatible with any plasmid delivery system such as lipofectins, cationic lipids, anionic lipids, liposomes, transfection agents, and cell targeting agents.

In a preferred embodiment, plasmid DNA is administered to an individual by intramuscular injection. In addition to plasmid DNA, the injectable composition may optionally comprise a facilitating such as bupivacaine or a related composition including those described in PCT Application Serial Number PCT/US94/00899, which is incorporated herein by reference.

In addition to use in plasmids, the constructs of the present invention may be useful in other genetic delivery systems in which DNA that encodes proteins whose expression is desired is transcribed in the nucleus, such as retroviruses or other viral or non-viral vectors.

EXAMPLE

Figure 2:
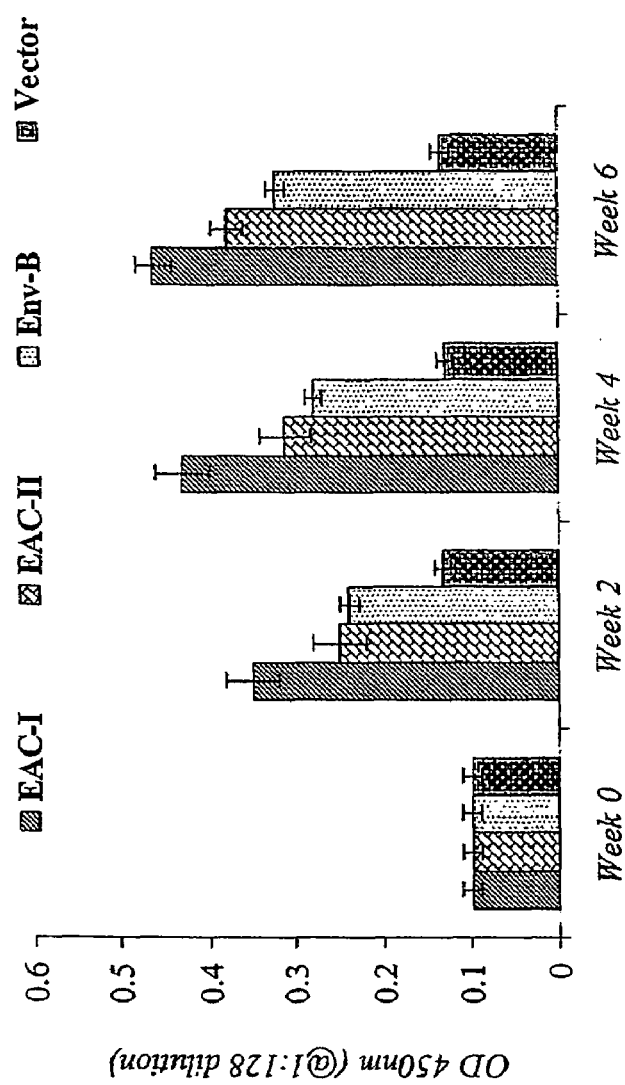
Figure 3:
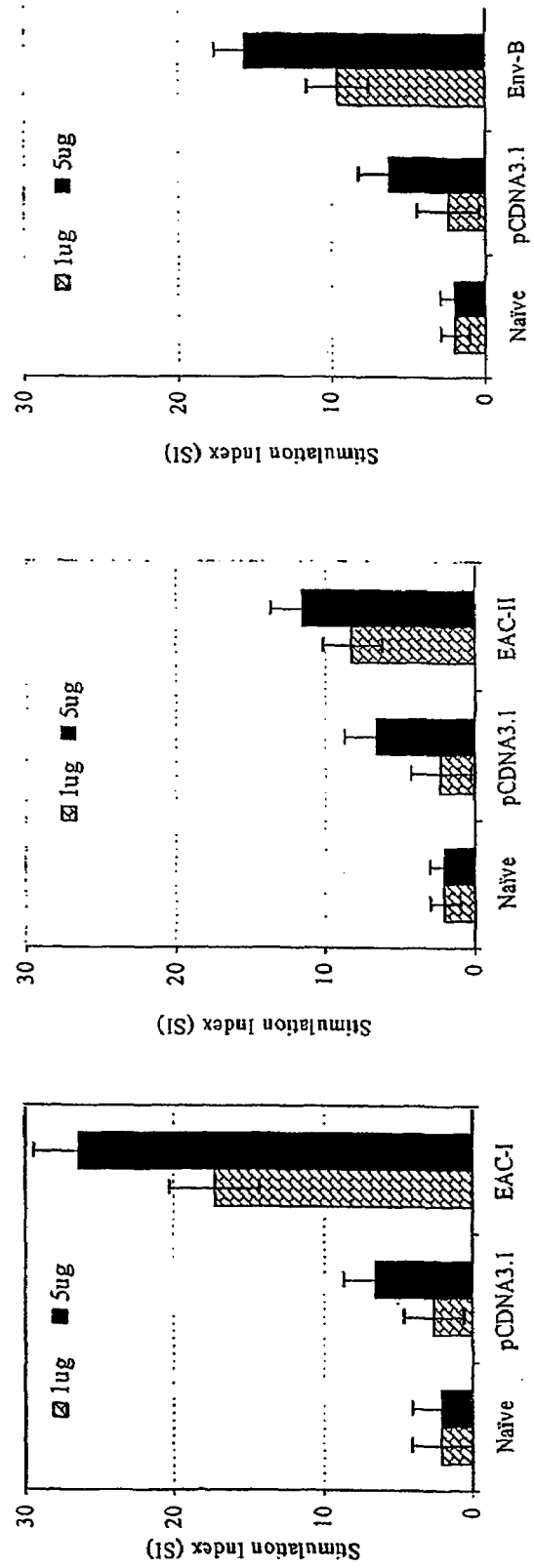
Figure 4:
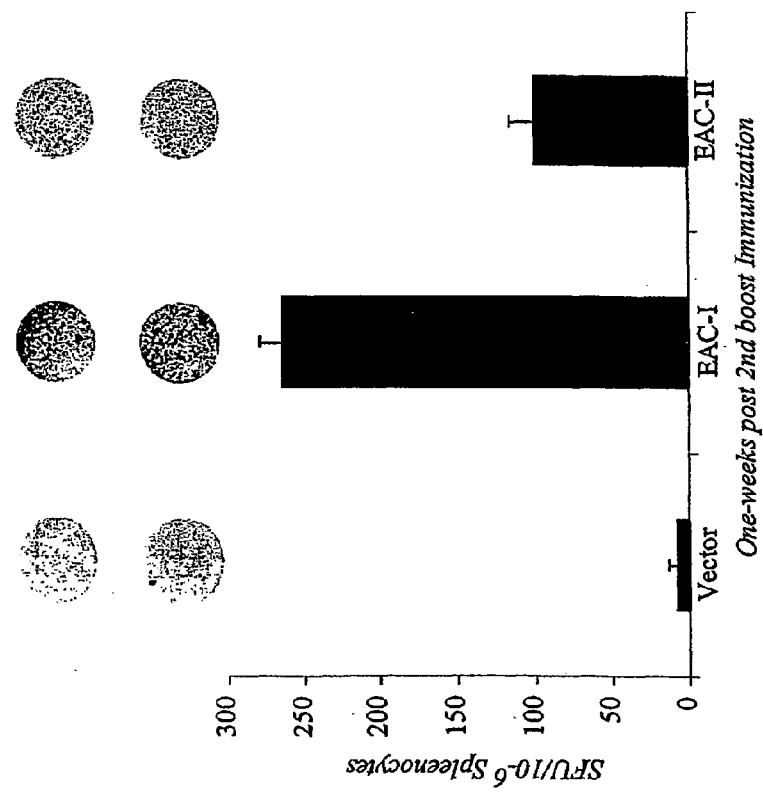
Figure 5:
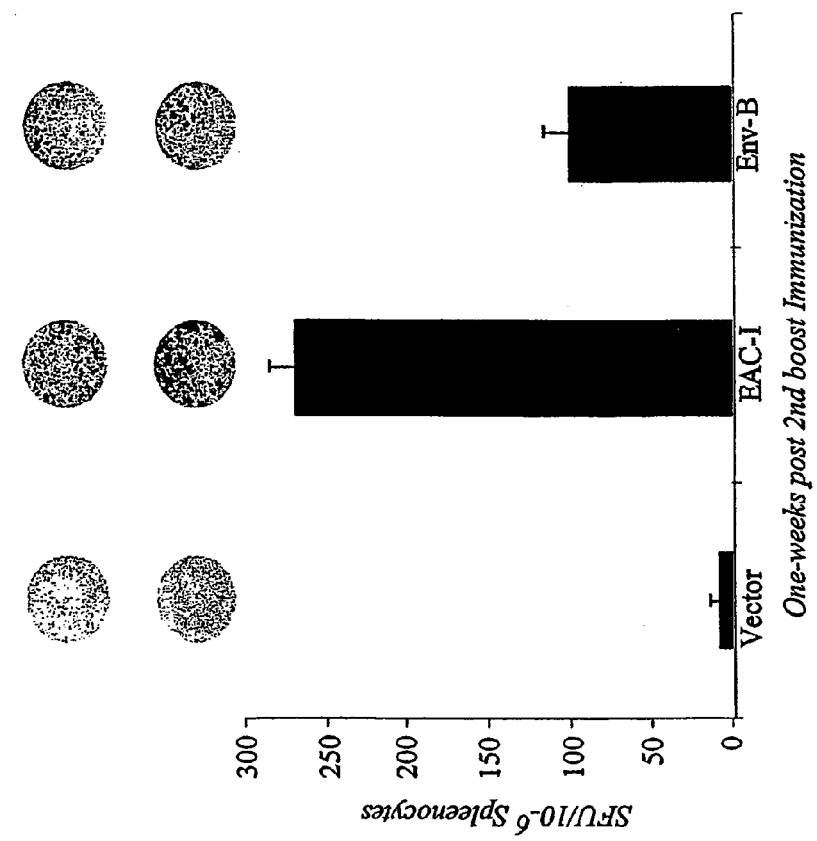

The data attached hereto in FIGS. 1-5 reports on a comparison of the immune responses against HIV-1 Env following administration of one of three plasmids, each of which encode Env. The Env coding sequence contains the RRE. The data clearly show that the combination of coding sequence for Env and Rev including a CTE yields an enhanced immune response relative to that observed following administration of a genetic construct that contains only coding sequence for Env and Rev or coding sequence for Env with a CTE.

What is claimed is:

1. A method of inducing an immune response against an immunogen in an individual comprising the step of administering to said individual either:
   a) a composition comprising a genetic construct that comprises
      i) coding sequence for HIV-1 Rev, and
      ii) coding sequence for said immunogen, wherein coding sequence for said immunogen comprises
         1) at least a portion of coding sequence for an HIV structural protein that includes an RRE and
         2) at least one CTE; or
   b) a composition comprising at least two nucleic acid molecules:
      i) at least one nucleic acid molecule comprises a coding sequence for HIV-1 Rev, and
      ii) at least one nucleic acid molecule comprises a coding sequence for an immunogen, wherein coding sequence for said immunogen comprises
         1) at least a portion of coding sequence for an HIV structural protein that includes an RRE and
         2) at least one CTE.

2. The method of claim 1 comprising the step of administering to said individual a composition comprising a genetic construct that comprises
   i) coding sequence for HIV-1 Rev, and
   ii) coding sequence for said immunogen, wherein coding sequence for said immunogen comprises
      1) at least a portion of coding sequence for an HIV structural protein that includes an RRE and
      2) at least one CTE.

3. The method of claim 1 comprising the step of administering to said individual a composition comprising at least two nucleic acid molecules:
   i) at least one nucleic acid molecule comprises a coding sequence for HIV-1 Rev, and
   ii) at least one nucleic acid molecule comprises a coding sequence for an immunogen, wherein coding sequence for said immunogen comprises
      1) at least a portion of coding sequence for an HIV structural protein that includes an RRE and
      2) at least one CTE.

4. A method of delivering a protein to an individual comprising the step of administering to said individual either:
   a) a composition comprising a genetic construct that comprises
      i) coding sequence for HIV-1 Rev, and
      ii) coding sequence for said protein, wherein coding sequence for said protein comprises
         1) at least a portion of coding sequence for an HIV structural protein that includes an RRE and
         2) at least one CTE; or
   b) a composition comprising at least two nucleic acid molecules:
      i) at least one nucleic acid molecule comprises a coding sequence for HIV-1 Rev, and
      ii) at least one nucleic acid molecule comprises a coding sequence for said protein, wherein coding sequence for said protein comprises
         1) at least a portion of coding sequence for an HIV structural protein that includes an RRE and
         2) at least one CTE.

5. The method of claim 4 comprising the step of administering to said individual a composition comprising a genetic construct that comprises
   i) coding sequence for HIV-1 Rev, and
   ii) coding sequence for said protein, wherein coding sequence for said protein comprises
      1) at least a portion of coding sequence for an HIV structural protein that includes an RRE and
      2) at least one CTE.

6. The method of claim 4 comprising the step of administering to said individual a composition comprising at least two nucleic acid molecules:
  i) at least one nucleic acid molecule comprises a coding sequence for HIV-1 Rev, and
  ii) at least one nucleic acid molecule comprises a coding sequence for said protein, wherein coding sequence for said protein comprises
    1) at least a portion of coding sequence for an HIV structural protein that includes an RRE and
    2) at least one CTE.

7. The method of claim 2 wherein the genetic construct is a DNA molecule.

8. The method of claim 7 wherein the genetic construct is a plasmid.

9. The method of claim 2 wherein the immunogen is a fusion protein comprising an HIV structural protein and at least one CTE.

10. The method of claim 2 wherein the immunogen is a fusion protein comprising at least a portion of an HIV structural protein and a non-HIV portion.

11. The method of claim 2 wherein the immunogen is a fusion protein comprising at least a portion of an HIV structural protein and an immunogenic non-HIV portion.

12. The method of claim 2 wherein the genetic construct comprises 1-5 CTEs.

13. The method of claim 3 wherein the at least two nucleic acid molecules are DNA molecules.

14. The method of claim 13 wherein the DNA molecules are plasmids.

15. The method of claim 3 wherein the immunogen is a fusion protein comprising an HIV structural protein and at least one CTE.

16. The method of claim 3 wherein the immunogen is a fusion protein comprising at least a portion of an HIV structural protein and a non-HIV portion.

17. The method of claim 3 wherein the immunogen is a fusion protein comprising at least a portion of an HIV structural protein and an immunogenic non-HIV portion.

18. The method of claim 3 wherein the coding sequence for the immunogen comprises 1-5 CTEs.

19. The method of claim 5 wherein the genetic construct is a DNA molecule.

20. The method of claim 19 wherein the genetic construct is a plasmid.

21. The method of claim 5 wherein the protein is an HIV structural protein that comprises at least one CTE.

22. The method of claim 5 wherein the protein is a fusion protein comprising at least a portion of an HIV structural protein and a non-HIV portion.

23. The method of claim 5 wherein the protein is a fusion protein comprising at least a portion of an HIV structural protein and an immunogenic non-HIV portion.

24. The method of claim 5 wherein the genetic construct comprises 1-5 CTEs.

25. The method of claim 6 wherein the at least two nucleic acid molecules are DNA molecules.

26. The method of claim 25 wherein the DNA molecules are plasmids.

27. The method of claim 6 wherein the protein is a fusion protein comprising an HIV structural protein and at least one CTE.

28. The method of claim 6 wherein the protein is a fusion protein comprising at least a portion of an HIV structural protein and a non-HIV portion.

29. The method of claim 6 wherein the protein is a fusion protein comprising at least a portion of an HIV structural protein and an immunogenic non-HIV portion.

30. The method of claim 6 wherein the coding sequence for the immunogen comprises 1-5 CTEs.

* * * * *